(12) United States Patent
Veasey et al.

(10) Patent No.: US 9,968,744 B2
(45) Date of Patent: *May 15, 2018

(54) PEN-TYPE INJECTOR

(71) Applicant: SANOFI-AVENTIS DEUTSCHLAND GMBH, Frankfurt am Main (DE)

(72) Inventors: Robert Frederick Veasey, Warwickshire (GB); Christopher Nigel Langley, Warwickshire (GB); Steven Wimpenny, Warwickshire (GB)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 0 days. days.

This patent is subject to a terminal disclaimer.

(21) Appl. No.: 15/296,381

(22) Filed: Oct. 18, 2016

(65) Prior Publication Data

US 2017/0028136 A1    Feb. 2, 2017

Related U.S. Application Data

(60) Continuation of application No. 13/208,486, filed on Aug. 12, 2011, which is a division of application No. (Continued)

(30) Foreign Application Priority Data

Mar. 3, 2003 (GB) .................................. 0304823.8

(51) Int. Cl.
*A61M 5/315* (2006.01)
*A61M 5/24* (2006.01)

(52) U.S. Cl.
CPC ...... *A61M 5/31501* (2013.01); *A61M 5/3155* (2013.01); *A61M 5/31526* (2013.01);
(Continued)

(58) Field of Classification Search
CPC .......... A61M 5/31526; A61M 5/31528; A61M 5/31533; A61M 5/31593; A61M 5/24;
(Continued)

(56) References Cited

U.S. PATENT DOCUMENTS 533,575 A   2/1895  Wilkens
4,865,591 A  9/1989  Sams
(Continued)

FOREIGN PATENT DOCUMENTS

CA   2138528 C   12/1998
CA   2359375 A1   7/2000
(Continued)

*Primary Examiner* — Shefali Patel
(74) *Attorney, Agent, or Firm* — McDonnell Boehnen Hulbert & Berghoff LLP

(57) ABSTRACT

The present invention relates to injectors, such as pen-type injectors, that provide for administration of medicinal products from a multidose cartridge and permit a user to set a delivery dose. An injector may include a housing, the cartridge containing a medicinal product, the cartridge being retained within the housing, a dose dial sleeve for selecting a dose of the medicinal product to be expelled, and a piston rod for expelling the selected dose of the medicinal product. The housing may be a unitary housing within which the dose dial sleeve for selecting the dose and the piston rod for expelling the selected dose are moveably retained. Alternatively, the injector may include the housing, the piston rod, an insert located in the housing and through which the piston rod may rotate, a ratchet, the dose dial sleeve, a drive sleeve, a button located on the drive sleeve and rotatable with respect to the drive sleeve, and a clutch which upon depression of the button prevents rotation between the dose dial sleeve and the drive sleeve.

10 Claims, 6 Drawing Sheets

Related U.S. Application Data

12/900,725, filed on Oct. 8, 2010, now Pat. No. 8,021,345, which is a continuation of application No. 10/790,025, filed on Mar. 2, 2004, now Pat. No. 7,905,867.

(52) U.S. Cl.
CPC .... *A61M 5/31528* (2013.01); *A61M 5/31533* (2013.01); *A61M 5/31541* (2013.01); *A61M 5/31593* (2013.01); *A61M 5/24* (2013.01); *A61M 5/3156* (2013.01); *A61M 5/31511* (2013.01); *A61M 5/31551* (2013.01); *A61M 5/31585* (2013.01); *A61M 2205/581* (2013.01); *A61M 2205/582* (2013.01)

(58) Field of Classification Search
CPC .... A61M 5/31; A61M 5/315; A61M 5/31501; A61M 5/31525; A61M 5/31535; A61M 5/31541; A61M 5/31545; A61M 5/31548; A61M 5/3155; A61M 5/31551; A61M 5/31565; A61M 5/31576; A61M 5/31583; A61M 5/3159; A61M 2205/581; A61M 2205/582
See application file for complete search history.

(56) References Cited

U.S. PATENT DOCUMENTS

| | | |
|---|---|---|
| 5,092,842 A | 3/1992 | Bechtold et al. |
| 5,226,895 A | 6/1993 | Harris |
| 5,226,896 A | 7/1993 | Harris |
| 5,279,586 A * | 1/1994 | Balkwill ............ A61M 5/3158 222/309 |
| 5,304,152 A | 4/1994 | Sams |
| 5,320,609 A | 6/1994 | Haber et al. |
| 5,378,233 A | 1/1995 | Haber et al. |
| 5,383,865 A | 1/1995 | Michel |
| 5,391,157 A | 2/1995 | Harris et al. |
| 5,480,387 A | 1/1996 | Gabriel et al. |
| 5,505,704 A | 4/1996 | Pawelka et al. |
| 5,582,598 A | 12/1996 | Chanoch |
| 5,584,815 A | 12/1996 | Pawelka et al. |
| 5,626,566 A | 5/1997 | Petersen et al. |
| 5,674,204 A | 10/1997 | Chanoch |
| 5,679,111 A | 10/1997 | Hjertman et al. |
| 5,688,251 A | 11/1997 | Chanoch |
| 5,807,346 A | 9/1998 | Frezza |
| 5,820,602 A | 10/1998 | Kovelman et al. |
| 5,851,079 A | 12/1998 | Horstman et al. |
| 5,921,966 A | 7/1999 | Bendek et al. |
| 5,957,896 A | 9/1999 | Bendek et al. |
| 5,961,495 A | 10/1999 | Walters et al. |
| 6,004,297 A | 12/1999 | Steenfeldt-Jensen et al. |
| 6,059,755 A | 9/2000 | Michel |
| 6,193,698 B1 | 2/2001 | Kirchhofer et al. |
| 6,221,046 B1 * | 4/2001 | Burroughs ........ A61M 5/31551 604/153 |
| 6,235,004 B1 * | 5/2001 | Steenfeldt-Jensen A61M 5/31551 604/207 |
| 6,248,095 B1 | 6/2001 | Giambattista et al. |
| 6,562,006 B1 | 5/2003 | Hjertman et al. |
| 6,613,023 B2 | 9/2003 | Kirchhofer et al. |
| 6,699,224 B2 | 3/2004 | Kirchhofer et al. |
| 6,899,698 B2 | 5/2005 | Sams |
| 6,932,794 B2 | 8/2005 | Giambattista et al. |
| 6,936,032 B1 | 8/2005 | Bush, Jr. et al. |
| 7,169,132 B2 | 1/2007 | Bendek et al. |
| 7,241,278 B2 | 7/2007 | Moller |
| 7,678,084 B2 | 3/2010 | Judson et al. |
| 7,850,662 B2 | 12/2010 | Veasey et al. |
| 8,187,233 B2 | 5/2012 | Harms et al. |
| 2002/0052578 A1 | 5/2002 | Moller |
| 2002/0120235 A1 | 8/2002 | Enggaard |
| 2002/0165499 A1 | 11/2002 | Slate et al. |
| 2003/0050609 A1 | 3/2003 | Sams |
| 2004/0059299 A1 | 3/2004 | Moller |
| 2004/0097883 A1 | 5/2004 | Roe |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0016143 A1 | 1/2007 | Miller et al. |
| 2009/0275916 A1 | 11/2009 | Harms et al. |

FOREIGN PATENT DOCUMENTS

| | | | |
|---|---|---|---|
| EP | 0496141 A1 | 7/1992 | |
| EP | 0897729 A2 | 2/1999 | |
| EP | 0937471 | 8/1999 | |
| EP | 0937476 | 8/1999 | |
| EP | 0937477 | 8/1999 | |
| EP | 1776975 A2 | 4/2007 | |
| WO | 91/14467 | 10/1991 | |
| WO | 93/07922 A1 | 4/1993 | |
| WO | WO 93/24160 | 12/1993 | |
| WO | 96/25965 | 8/1996 | |
| WO | 99/38554 | 8/1999 | |
| WO | 01/10484 | 2/2001 | |
| WO | WO 0110484 A1 * | 2/2001 | ........ A61M 5/31551 |
| WO | 02/30495 A2 | 4/2002 | |
| WO | 02/053214 | 7/2002 | |
| WO | 02/092153 | 11/2002 | |
| WO | 03/080160 | 10/2003 | |
| WO | 2006/084876 A1 | 8/2006 | |

* cited by examiner

PEN-TYPE INJECTOR

CROSS REFERENCE TO RELATED APPLICATIONS

This application is a continuation of application Ser. No. 13/208,486, filed Aug. 12, 2011, which is a division of application Ser. No. 12/900,725, filed on Oct. 8, 2010, now U.S. Pat. No. 8,021,345, which is a continuation of application Ser. No. 10/790,025, filed on Mar. 2, 2004, now U.S. Pat. No. 7,905,867, which claims priority to Great Britain Patent Application No. 0304823.8, filed on Mar. 3, 2003, the entire contents of which are incorporated herein by reference.

BACKGROUND

The present invention relates to pen-type injectors, that is to injectors of the kind that provide for administration by injection of medicinal products from a multidose cartridge. In particular, the present invention relates to such injectors where a user may set the dose.

Such injectors have application where regular injection by persons without formal medical training occurs. This is increasingly common amongst those having diabetes where self-treatment enables such persons to conduct effective management of their diabetes.

These circumstances set a number of requirements for pen-type injectors of this kind. The injector must be robust in construction, yet easy to use both in terms of the manipulation of the parts and understanding by a user of its operation. In the case of those with diabetes, many users will be physically infirm and may also have impaired vision. Where the injector is to be disposable rather than reusable, the injector should be cheap to manufacture and easy to dispose of (preferably being suitable for recycling).

SUMMARY

It is an advantage of the present invention that an improved pen-type injector is provided.

According to first aspect of the present invention, a pen-type injector comprises a housing;
 a cartridge containing medicinal product, the cartridge being retained within the housing;
 means for selecting a dose of medicinal product to be expelled; means for expelling the selected dose of medicinal product;
 characterised in that the housing comprises a unitary housing within which the dose selecting means and the dose expelling means are moveably retained.

It is an advantage of this aspect of the invention that it affords a more robust construction of a pen-type injector.

According to a second aspect of the present invention, a pen-type injector comprises
 a piston rod having a screw thread;
 an insert located in the housing and through which the piston may rotate; ratchet means associated with the insert to ensure the piston only rotates in a single direction through the insert;
 a dose dial sleeve rotatable with respect to the housing and the insert;
 a drive sleeve which is axially displaceable but not rotatable with respect to the piston rod;
 a button located on the drive sleeve and rotatable with respect to the drive sleeve; and
 clutch means which upon depression of the button prevents rotation between the dose dial sleeve and the drive sleeve.

Preferably, the injector further comprises a nut rotatable with respect to the drive sleeve and axially displaceable but not rotatable with respect to the dose dial sleeve.

Preferably, the insert comprises a web having an opening, a first cylindrical portion extending from a first side of the web, a second cylindrical portion extending from a second side of the web and a third cylindrical portion extending from a second side of the web.

Alternatively, the insert comprises a web having an opening, a first cylindrical portion extending from a first side of the web, a boss provided on a second side of the web and a cylindrical portion extending away from the web about a periphery of the boss.

In a second alternative, the insert comprises a web having an opening, a first cylindrical portion extending from a first side of the web, a boss provided on a second side of the web, a radial flange extending from the boss, the radial flange being spaced from the web, and a cylindrical portion extending away from the web about a periphery of the radial flange.

Preferably, the dose dial sleeve comprises a first section of first diameter and a second section of second diameter, the insert and an inner surface of the first section being provided with inter-engaging features to provide a helical thread between the insert and the dose dial sleeve.

Alternatively the dose dial sleeve comprises a first cylindrical portion rigidly connected to a second generally cylindrical portion, an inner surface of the first section and an outer surface of the cylindrical portion of the insert are provided with inter-engaging features to provide a helical thread between the insert and the dose dial sleeve.

More preferably, the second generally cylindrical portion comprises a first cylindrical section and a second cylindrical section connected by a shoulder, the first section being rigidly keyed to an inner surface of the first portion of the dose dial sleeve, and the second section being of the same outer diameter as the housing.

Alternatively the second generally cylindrically portion comprises a first cylindrical section and a second cylindrical section connected by a radial flange extending from a part of the second section, the first section being rigidly keyed to an inner surface of the first portion of the dose dial sleeve, and the second section being of the same outer diameter as the housing.

Preferably, an outer surface of the dose dial sleeve is provided with graphics and the housing is provided with an aperture or window through which a portion of the graphics may be viewed.

Preferably, the drive sleeve comprises a first part of first diameter located between the insert and the piston rod and a second part of second diameter located between the piston rod and the dose dial sleeve, an internal surface of the drive sleeve being splined to the piston rod such that no relative rotation may occur between these parts, only longitudinal displacement.

More preferably, the central receiving area includes at a first end a centrally located domed part.

Preferably, the nut is provided on a helical thread provided on the drive sleeve and is located between the drive sleeve and the dose dial sleeve, the dose dial sleeve and the nut being splined together by spline means to prevent relative rotation between the nut and the dose dial sleeve.

Preferably, the drive sleeve further comprises a central receiving area having a peripheral recess, the button being of generally "T" shaped configuration has a stem that is retained within the receiving area by co-operation between a peripheral bead provided on the stem retained in a peripheral recess provided in the central receiving area.

More preferably the second end of the piston rod is generally U-shaped, each of the limbs of the U-shape being received within a second part of the drive sleeve.

Preferably, the clutch means comprises a plurality of radially extending longitudinally directed teeth provided respectively on the dose dial sleeve and the drive sleeve.

Preferably, clicker means are provided between the dose dial sleeve and the drive sleeve, the clicker means comprising a plurality of longitudinally extending teeth and a flexible toothed member, one of the plurality of teeth and the toothed member being provided on the dose dial sleeve, the other being provided on the drive sleeve, relative rotation between the dose dial sleeve and the drive sleeve causing the flexible toothed member to ride over the teeth to produce a series of clicks.

According to a third aspect of the present invention, a pen-type injector comprises a housing;
 a piston rod having a screw thread;
 an insert located in the housing and through which the piston may rotate;
 a dose dial sleeve rotatable with respect to the housing and the insert; and
 a drive sleeve which is axially displaceable with respect to the housing;
 characterized in that a maximum angular displacement of the dose dial sleeve with respect to the housing is determined by abutment of a radially directed lug on the dose dial sleeve with a catch means on the insert.

Preferably, the radially directed lug extends parallel to a longitudinal axis of the dose dial sleeve.

Preferably, the catch means comprises a groove extending about a central land, the central land being wedge shaped such that a first edge extends radially less far than a second opposite edge to define a sloping surface between the first edge and the second edge.

BRIEF DESCRIPTION OF THE FIGURES

The invention will now be described, by way of example only, with reference to the accompanying drawings, in which.

DETAILED DESCRIPTION

Figure 1:
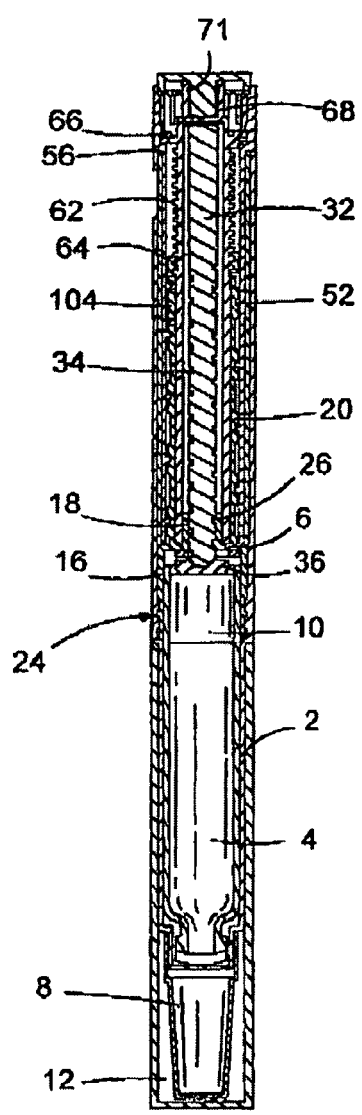
FIG. 1 shows a sectional side view of a first embodiment of an injector in accordance with the present invention in a first position.
Figure 2:
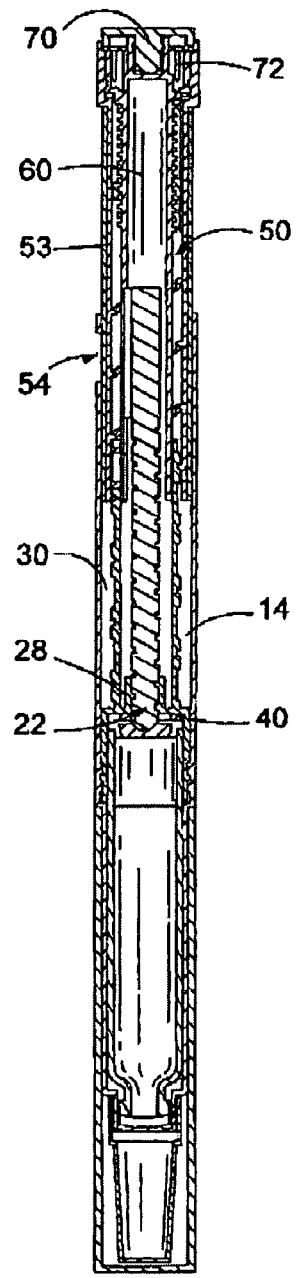
FIG. 2 shows a sectional side view of the injector of FIG. 1 in a second position.

Referring first to FIGS. 1 to 5 there may be seen an injector in accordance with a first embodiment of the present invention. The injector comprises a housing 2 within which are located a cartridge 4 containing a medicinal product, means for setting or selecting the dose of medicinal product to be expelled and means for expelling the selected dose of medicinal product. The housing 2 is generally cylindrical in shape and is divided into two compartments by a web 6 to be described in more detail below. The cartridge 4 is located within a first part of the housing 2. The dose setting means and the means for expelling the selected dose of medicinal product are retained, that is held, within a second part of the housing 2. An advantage of a one piece housing enclosing the cartridge 4 together with the dose setting and dose expelling means lies in the ease of assembly of the product. This is in part due to the reduced number of components in the pen-type injector. Also, the unitary nature of the housing 2 means that the pen-type injector is more robust.

The cartridge 4 may be secured in position in the first part of the housing 2 by any suitable means. A needle unit may be secured to a first end of the cartridge 4. A temporary covering 8 is shown in this position in the Figures. The cartridge 4 further comprises a displaceable piston 10.

Advancing the piston 10 towards the first end of the cartridge 4 causes the medicinal product to be expelled from the cartridge 4 through the needle unit. A cap 12 is provided to cover the needle unit when the injector is not in use. The cap 12 may be releasably secured to the housing 2 by any suitable means.

The dose setting means and the means for expelling the selected dose of medicinal product will now be described in more detail. The web 6 dividing the housing 2 is a part of an insert 14 located within the housing 2. The insert 14 comprises a first cylindrical portion 16 extending from a first side of the web 6 and second and third cylindrical portions 18,20 extending from a second side of the web 6. The web 6 is provided with a circular opening 22 extending through the web 6.

The first cylindrical portion 16 extends from a periphery of the web 6. The insert 14 is secured to the housing 2 by way of the first cylindrical portion 16 by any suitable means. In the illustrated embodiment features 24 are provided within the housing 2 and on an outer surface of the first cylindrical portion 16 to enable the insert to be a snap fit to the housing 2.

The second cylindrical portion 18 extends a small distance from the second side of the web 6 about a periphery of the opening 22. An internal surface of the second cylindrical portion is provided with a screw thread 26.

The third cylindrical portion 20 extends substantially within the housing 2 from the second side of the web 6. The diameter of the third cylindrical portion 20 is such that a first channel 28 is formed between an outer surface of the second cylindrical portion 20 and an inner surface of the third cylindrical portion. A second channel 30 is formed between an outer surface of the third cylindrical portion 20 and the housing 2.

A piston rod 32 is provided extending through the opening in the web 6. The piston rod 32 is generally elongate and is provided with a screw thread 34 extending from a first end of the piston rod 32. The screw thread 34 of the piston rod 32 engages the screw thread of the inner surface of the second cylindrical portion 18 of the insert 14. The first end of the piston rod 32 is provided with a pressure foot 36. In use the pressure foot 36 is disposed on the first side of the web 6 to abut the cartridge piston 10.

Ratchet means 40 are located adjacent the web 6 on the first side of the web 6. The ratchet means 40 serve the purpose of allowing the piston rod 32 only to rotate through the insert 14 in a single direction. Due to the one piece construction of the housing, the ratchet means can be made larger than in known devices and so is stronger (more rigid).

A dose dial sleeve 50 of generally cylindrical form comprises a first section of first diameter and a second section of second diameter. The first section is located within the second channel 30. An inner surface of the first section and the outer surface of the third cylindrical portion 20 are provided with inter-engaging features to provide a helical thread 52 between the insert 14 and the dose dial sleeve 50. Conveniently as in the illustrated embodiment, this is achieved by a helical track provided on the outer surface of the third cylindrical portion 20 within which a helical rib provided on the inner surface of the dose dial sleeve 50 may run. This enables the dose dial sleeve 50 to rotate about and along the third cylindrical portion 20 of the insert 14.

An outer surface of the first section of the dose dial sleeve 50 is provided with graphics 53. The graphics are typically a sequence of reference numerals. The housing 2 is provided with an aperture or window 54 through which a portion of the graphics, representing a dosage value selected by the user, may be viewed.

The graphics 53 may be applied to the dose dial sleeve 50 by any suitable means. In the illustrated embodiment, the graphics 53 are provided in the form of a printed label encircling the dose dial sleeve 50. Alternatively the graphics may take the form of a marked sleeve clipped to the dose dial sleeve 50. The graphics may be marked in any suitable manner, for example by laser marking.

It is an advantage of this arrangement that the helical thread 52 is formed within the dose dial sleeve between the dose dial sleeve and the insert, As can be seen this means there is no direct route from outside the injector to the working surfaces of the helical thread. Should dust or dirt enter the pen this will tend to occur between the housing and the dose dial sleeve where there are no working parts with which to interfere. This is not the case for known devices in which a helical thread is formed between the housing and an interior moving surface. In addition because of the narrower diameter of the helical thread 52 formed between the dose dial sleeve and the drive sleeve in comparison to a similar thread formed between the housing and the dose dial sleeve, the helical thread 52 is more efficient and easier to overhaul. This arrangement also produces an improvement in the dose size that can be delivered for a particular linear travel of the dose expelling means.

The second section of the dose dial sleeve 50 is preferably of the same outer diameter as the housing 2. Within the dose dial sleeve 50 there is a shoulder 56 between the first section of the dose dial sleeve 50 and the second section of the dose dial sleeve 50.

A drive sleeve 60 of generally cylindrical form comprises a first part of first diameter and a second part of second diameter. A first end of the first part is located within the first channel 28 of the insert 14 in the position shown in FIG. 1. The first part of the drive sleeve 60 may be considered as comprising a first portion aligned with a second portion. More generally in the position shown in FIG. 1 the first portion of the drive sleeve 60 is located between the insert 14 and the piston rod 32 while the second portion is located between the piston rod 32 and the dose dial sleeve 60.

A second end of the piston rod 32 and an internal surface of the drive sleeve 60 are splined together such that no relative rotation may occur between these parts, only longitudinal displacement.

The outer surface of the second portion of the first part of the drive sleeve 60 is provided with a helical thread 62. A nut 64 is provided on the helical thread 62 between the drive sleeve 60 and the dose dial sleeve 50. The dose dial sleeve 50 and the nut 64 are splined together by spline means to prevent relative rotation between the nut 64 and the dose dial sleeve 50.

The second part of the drive sleeve 60 is of larger diameter than the first part of the drive sleeve 60. There is a step 66 between the first part of the drive sleeve 60 and the second part. The second part of the drive sleeve 60 is seated within the second section of the dose dial sleeve 50. The shoulder 56 of the dose dial sleeve 50 and the step 66 of the drive sleeve 60 are adapted to be releasably engagable with one another to form a clutch means. When, as in FIG. 1, the dose dial sleeve 50 and the drive sleeve 60 are not in engagement the dose dial sleeve 50 is able to rotate with respect to the drive sleeve 60. Conveniently, the clutch means comprises a plurality of radially extending longitudinally directed teeth provided respectively on the shoulder 56 of the dose dial sleeve 50 and the step 66 of the drive sleeve 60. When the dose dial sleeve 50 and the drive sleeve 60 are not forced together the respective teeth will ride over one another. Preferably, the radial separation of the respective teeth corresponds to a unit dosage.

The second part of the drive sleeve 60 further comprises a central receiving area 68 having a peripheral recess. A button 70 of generally "T" shaped configuration is provided, the stem of which is retained within the receiving area. The stem of the button 70 is provided with a peripheral bead 71 that is retained in the peripheral recess, the button 70 being able freely to rotate with respect to the drive sleeve 60, but being retained axially therewith.

Clicker means are provided between the second section of the dose dial sleeve 50 and the second part of the drive sleeve 60. In the illustrated embodiment, the internal surface of the second section of the dose dial sleeve 50 is provided with a plurality of longitudinally extending teeth. The radial separation of the teeth preferably corresponds to a unit dosage. The second part of the drive sleeve 60 carries a flexible toothed member 72. Relative rotation between the dose dial sleeve 60 and the drive sleeve 60 will cause the flexible toothed member 72 to ride over the teeth to produce a series of clicks.

In FIG. 1, the injector is provided with a filled cartridge 4. To operate the injector a user must first select a dose. To set a dose the dose dial sleeve 50 is rotated by manipulating the second section of the dose dial sleeve 50 with respect to the housing 2 until the desired dose value is visible through the window 54. This action draws the dose dial sleeve 60 along the second cylindrical portion of the insert 14, The drive sleeve 60 cannot rotate since it is splined to the piston rod 32. The piston rod 32 does not rotate due to the action of the ratchet means 40. The drive sleeve 60 is carried away from the web 6 along the piston rod 32 by the dose dial sleeve 50 as the dose dial sleeve 50 moves out from the housing 2. The relative rotation between the dose dial sleeve 50 and the drive sleeve 60 causes the flexible toothed member 72 to ride over the ridges in the drive sleeve 60 to create a series of clicks. This is an audible confirmation of the dose being dialed.

Since the nut 64 is splined to the dose dial sleeve 50, the relative rotation between the dose dial sleeve 50 and the drive sleeve 60 causes the nut 64 to progress along the helical thread 62 of the drive sleeve 60.

Figure 3:
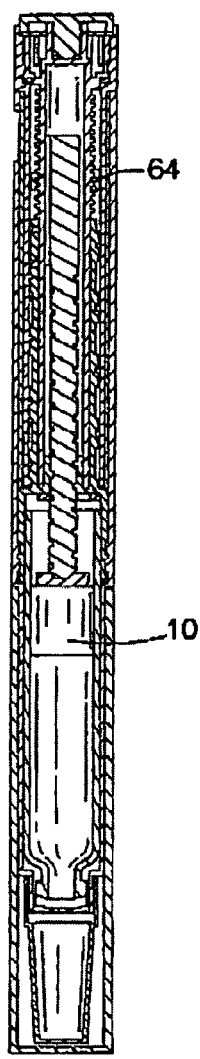
FIG. 3 shows a sectional side view of the injector of FIG. 1 in a third position.

Once a desired dose has been set (as shown for example in FIG. 2), to deliver the dose the user depresses the button 70 to urge the button 70 towards the first end of the housing 2. When the button 70 is depressed the second part of the drive sleeve 60 is driven into the second section of the dose dial sleeve 50 to engage the clutch means therebetween to prevent relative rotation between the dose dial sleeve 50 and the drive sleeve 60. The drive sleeve 60 may still rotate with respect to the button 70. Further longitudinal movement of the button 70 causes the dose dial sleeve 50 (together with the drive sleeve 60) to rotate towards the first end of the injector. Since the piston rod 32 is splined to the drive sleeve 60, the piston rod 32 is also rotated through the insert 14 and the ratchet means 40 towards the first end of the injector, thereby to advance the cartridge piston 10 and expel the desired dose of medicinal product. The piston rod 32 continues to advance until the drive sleeve 60 and dose dial sleeve 50 have returned to their initial positions (FIG. 3).

It can be seen that the dose selecting means and the dose expelling means extend beyond a second end of the housing 2 as the dose is selected and are returned within the housing 2 as the selected dose is expelled.

Figure 4:
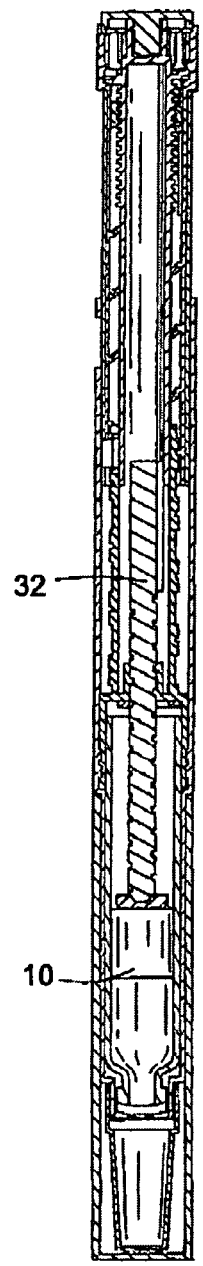
FIG. 4 shows a sectional side view of the injector of FIG. 1 in a fourth position.
Figure 5:
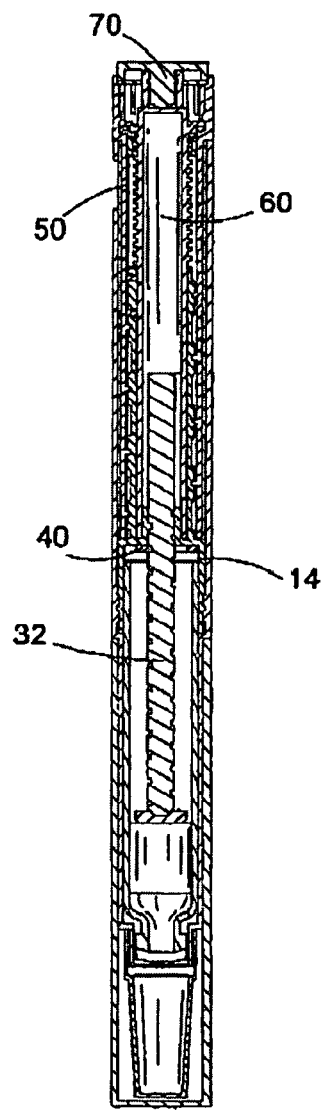
FIG. 5 shows a sectional side view of the injector of FIG. 1 in a second position.

Further dosages may be delivered as required. FIG. 4 shows an example of a subsequently selected dosage. It will be noted that the nut 64 has advanced further along the helical thread 62 of the drive sleeve 60. The position of the nut 64 along the helical thread 62 corresponds to the amount of medicinal product remaining in the cartridge 4, such that when the nut 64 reaches the end of the helical thread 62 (in the illustrated embodiment adjacent to the step 66 of the drive sleeve 60) and can rotate no further this corresponds to no medicinal product remaining in the cartridge 4. It will be seen that if a user seeks to select a quantity of medical product greater than that remaining in the cartridge 4, this cannot be done since when the nut 64 stops rotating the dose dial sleeve 50 and the drive sleeve 60 will become locked together preventing rotation of the dose dial sleeve 50 and setting of a larger dose. FIG. 5 shows an injector according to the present invention in which the entire medical product within the cartridge 4 has been expelled.

Figure 6:
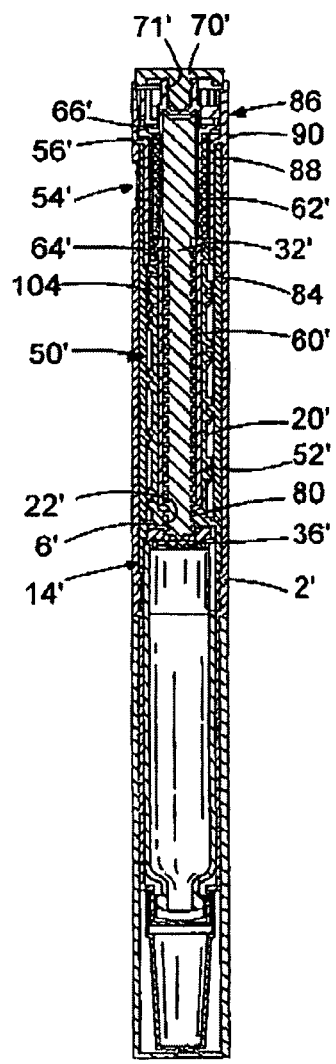
FIG. 6 shows a sectional side view of a second embodiment of an injector in accordance with the present invention.

A second embodiment of the present invention is disclosed in FIG. 6. Like reference numerals are used to refer to like parts as between the first and second embodiments.

The piston rod 32' shown in FIG. 6 has a dual start thread. The piston foot 36' is reversible. This has advantages in manufacture. As can be seen the structure of the insert 14' has been revised. The first side of the web 6' is substantially unchanged. The other side of the web is now provided with a boss 80. A cylindrical portion 20' extends away from the web 6' about a periphery of the boss 80. Threaded opening 22' extends through the web 6' and the boss 80. An end of the cylindrical portion 20' of the insert 14' remote from the web 6' is provided with a stop in the form of a land 104.

The dose dial sleeve 50' is of modified construction. The dose dial sleeve comprises a first cylindrical portion 84 rigidly connected to a second generally cylindrical portion 86. An inner surface of the first cylindrical portion 84 and the outer surface of the cylindrical portion 20' of the insert 14' are provided with interengaging features to provide a helical thread 52' between the insert 14' and the dose dial sleeve 50'. An outer surface of the first cylindrical portion 84 is provided with the dose graphics. The housing 2' is provided with an aperture or window 54' through which a portion of the graphics may be viewed.

The second generally cylindrical portion 86 comprises a first cylindrical section 88 and a second cylindrical section 90. The first section 88 is rigidly keyed to an inner surface of the first portion 84 of the dose dial sleeve 50'. The second section 90 is preferably of the same outer diameter as the housing 2'. Within the dose dial sleeve 50' there is a shoulder 56' between the first section 86 and the second section 90.

A nut 64' is provided on the helical thread 62' between the drive sleeve 60' and the first cylindrical section 88 of the dose dial sleeve 50'. The first cylindrical section 88 and the nut 64' are splined together by spline means to prevent relative rotation between the nut 64' and the dose dial sleeve 50'.

The shoulder 56' of the dose dial sleeve 50' and a step 66' of a drive sleeve 60' are adapted to be releasably engagable with one another to form a clutch means. When, as in FIG. 6, the dose dial sleeve 50' and the drive sleeve 60' are not in engagement the dose dial sleeve 50' is able to rotate with respect to the drive sleeve 60'. Conveniently, the clutch means comprises a plurality of radially extending longitudinally directed teeth provided respectively on the shoulder 56' of the dose dial sleeve 50' and the step 66' of the drive sleeve 60'. When the dose dial sleeve 50' and the drive sleeve 60' are not forced together the respective teeth will ride over one another.

It will be seen that the structure of the drive sleeve 60' has also been modified. The second end of the piston rod 32' is provided with a scooped surface within which a domed part 90 of the drive sleeve 60' may extend. The domed part 90 is centrally located within a second part of the drive sleeve 60' at a first end of the receiving area.

The button 70' is of generally "T" shaped configuration. The stem of the button 70' is retained within the receiving area. The stem of the button 70' is provided with a peripheral bead 71' that is retained in the peripheral recess, the button 70' being able freely to rotate with respect to the drive sleeve 60', but being retained axially therewith.

When the button 70' is depressed the drive sleeve 60' is urged into contact with the dose dial sleeve 50' such that the clutch means are engaged. At the same time, the scooped surface of the piston rod 32' and the domed surface of the drive sleeve approach but do not contact one another. The advantage of this structure is that it enables the overall length of the device to be reduced thereby enabling easier operation of the device when expressing fluid from a cartridge.

Figure 7:
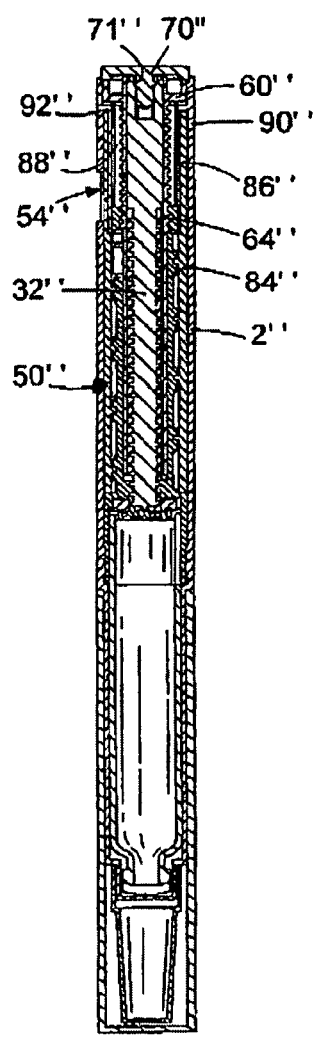
FIG. 7 shows a sectional side view of a third embodiment of an injector in accordance with the present invention.

A further embodiment of the button 70" and the dose dial sleeve 50" can be seen in FIG. 7. Again like reference numerals are used to refer to like parts. In the embodiment of FIG. 7, the overall length of the device may be reduced still further. The second end of the piston rod 32" is generally U-shaped. The limbs of the U-shape are received within a second part of the drive sleeve 60". A central receiving area of the drive sleeve 60" is defined by limbs (not shown) located in use between the limbs formed on the second end of the piston rod 32". The button 70" is of generally "T" shaped configuration. The stem of the button 70" is retained within the receiving area. The stem of the button 70" is provided with a peripheral bead 71" that is retained in the peripheral recess, the button 70" being able freely to rotate with respect to the drive sleeve 60", but being retained axially therewith.

The second generally cylindrically portion 86" of the dose dial sleeve 50" comprises a first cylindrical section 88" and a second cylindrical section 90" connected by a radial flange 92 extending from a part of the second section, the first section 88" being rigidly keyed to an inner surface of the first portion 84" of the dose dial sleeve 50", and the second section 90" being of the same outer diameter as the housing 2".

Figure 8:
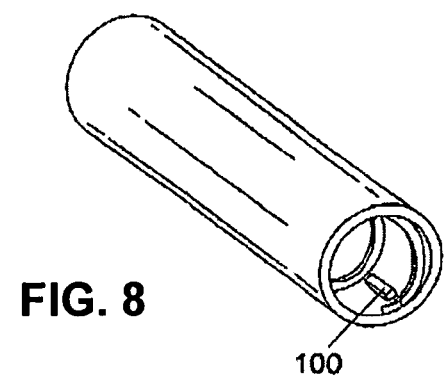
FIG. 8 shows a perspective view of a dose dial sleeve for use in conjunction with the present invention.
Figure 9:
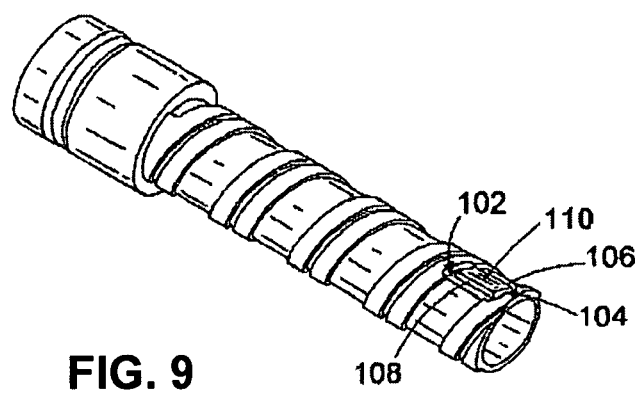
FIG. 9 shows a perspective view of an insert for use with the dose dial sleeve of FIG. 8.

In each of FIGS. 6 and 7, there is a further modification to each of the dose dial sleeve and the insert. This may be seen more clearly with reference to FIGS. 8 and 9.

At a first end of the dose dial sleeve there is located on an internal surface a radially directed lug 100 extending generally parallel to a longitudinal axis of the sleeve. At a second end of the insert on an external surface thereof there is provided a catch means. The catch means comprises a groove 102 extending about a central land 104. The central land 104 is generally wedge shaped such that a first edge 106 nearer the start of the thread extends radially less far than a second opposite edge 108 located further along the thread. A sloping surface 110 is defined between the first edge 106 and the second edge 108. Thus, when the dose dial sleeve is assembled to the insert, by threading the dose dial sleeve onto the insert, the lug 100 passes over the first edge 106 and over the sloping surface 110. As the lug 100 passes fully over the land 104 some elastic deformation of the respective elements, the dose dial sleeve and the insert occurs. Once the lug 100 is over the land 104, the second edge 108 of the land 104 acts as a stop to prevent removal of the dose dial sleeve from the insert.

The location of the second edge 108 of the land 104 is conveniently chosen at a radial location corresponding to 80 units of medicinal product, that is the maximum dose available is 80 units when the dose dial sleeve is wound from the initial position shown in any of FIG. 1, 6 or 7 to a fully extended position with the second edge 108 of the land 104 contacting the lug 100.

Figure 10:
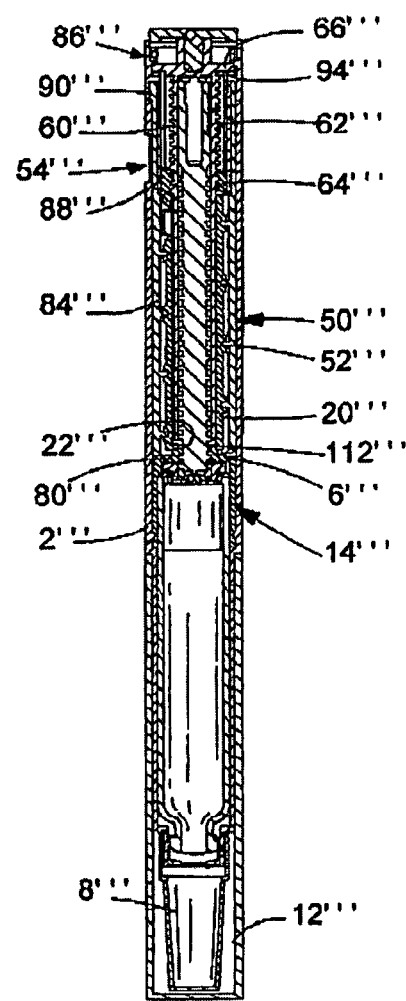
FIG. 10 shows a sectional side view of a fourth embodiment of an injector in accordance with the present invention.

A fourth embodiment of the present invention is disclosed in FIG. 10. Like reference numerals are used to refer to like parts.

As can be seen the structure of the insert 14" has been revised. The first side of the web 6" is substantially unchanged. The other side of the web is now provided with a boss 80'. A radial flange 112 extends outwardly from the boss 80", the radial flange 112 being spaced from the web 6", and a cylindrical portion 20' extending away from the web 6" about a periphery of the radial flange 110. A threaded opening 22' extends through the web 6" and the boss 80".

The dose dial sleeve 50' is of modified construction. The dose dial sleeve 50' comprises a first cylindrical portion 84" rigidly connected to a second generally cylindrical portion 86". An inner surface of the first portion 84' and the outer surface of the cylindrical portion 20" of the insert 14" are provided with inter-engaging features to provide a helical thread 52" between the insert 14" and the dose dial sleeve 50". An outer surface of the first cylindrical portion 84" is provided with the dose graphics. The housing 2' is provided with an aperture or window 54' through which a portion of the graphics may be viewed.

The second generally cylindrical portion 86" comprises a first inner cylindrical section 88" and a second outer cylindrical section 90". The first section 88" is rigidly keyed to an inner surface of the first portion 84' of the dose dial sleeve 50'. The second section 90' is preferably of the same outer diameter as the housing 2". Within the dose dial sleeve 50" there is a radial flange 94 extending between the outer section 90" and an intermediate part of the inner section 88".

A nut 64" is provided on a helical thread 62' formed on the drive sleeve 60". The nut 64" is disposed between the drive sleeve 60" and the second cylindrical section 88" of the dose dial sleeve 50". The second cylindrical section 88" and the nut 64" are keyed together by spline means to prevent relative rotation between the nut 64" and the dose dial sleeve 50".

An upper surface of the radial flange 94 of the dose dial sleeve 50' and a step 66' of the drive sleeve 60" are adapted to be releasably engagable with one another to form a clutch means. When, as in FIG. 10, the dose dial sleeve 50" and the drive sleeve 60" are not in engagement the dose dial sleeve 50" is able to rotate with respect to the drive sleeve 60". Conveniently, the clutch means comprises a plurality of radially extending longitudinally directed teeth provided respectively on the radial flange 94 of the dose dial sleeve 50' and the step 66' of the drive sleeve 60". When the dose dial sleeve 50" and the drive sleeve 60" are not forced together the respective teeth will ride over one another.

The invention claimed is:

1. A drug delivery device, comprising:
   a housing;
   a dose dial sleeve provided with a plurality of teeth on an internal surface;
   a drive sleeve carrying a toothed member configured to ride over the plurality of teeth of the dose dial sleeve;
   a piston rod coupled to the drive sleeve;
   a ratchet configured to prevent rotation of the piston rod during dose selection and that the piston rod in turn prevents rotation of the drive sleeve during the dose selection; and
   a nut located between the drive sleeve and the dose dial sleeve, where the nut moves axially relative to the housing during the dose selection,
   wherein the drive sleeve is prevented from rotating with the dose dial sleeve during the dose selection and the dose dial sleeve rotates together with the drive sleeve during dose delivery.

2. The drug delivery device according to claim 1, wherein relative rotation between the dose dial sleeve and the drive sleeve will cause the toothed member to ride over the plurality of teeth of the dose dial sleeve.

3. The drug delivery device according to claim 1, further comprising a button, wherein
   when the button is pressed, the drive sleeve is driven into the dose dial sleeve to prevent relative rotation between the dose dial sleeve and the drive sleeve.

4. The drug delivery device according to claim 1, wherein the piston rod is configured to advance during the dose delivery until the drive sleeve and the dose dial sleeve have returned to an initial position.

5. The drug delivery device according to claim 4, wherein the piston rod has a screw thread.

6. The drug delivery device according to claim 1, comprising a medicinal product in a cartridge.

7. The drug delivery device according to claim 6, where an axial position of the nut after the movement of the nut during the dose selection corresponds to an amount of the medicinal product remaining in the cartridge.

8. The drug delivery device according to claim 1, wherein an outer surface of the dose dial sleeve includes graphics and wherein the housing is provided with an aperture or a window through which a portion of the graphics may be viewed.

9. The drug delivery device according to claim 1, wherein the dose dial sleeve comprises a first cylindrical portion rigidly connected to a second cylindrical portion.

10. The drug delivery device according to claim 1, wherein the axial movement of the nut is prevented during the dose selection when a user of the drug delivery device attempts to set a dose greater than an amount of a medicinal product remaining in the drug delivery device.

* * * * *